United States Patent [19]

Bergamin et al.

[11] Patent Number: 4,808,735

[45] Date of Patent: Feb. 28, 1989

[54] PROCESS FOR THE REDUCTION OF THE KETENE TRIMER CONTENT IN RAW DIKETENE

[75] Inventors: Renzo Bergamin, Raron; Wilhelm Quittmann, Visp, both of Switzerland

[73] Assignee: Lonza Ltd., Gampel/Valais, Switzerland

[21] Appl. No.: 177,609

[22] Filed: Apr. 5, 1988

[30] Foreign Application Priority Data

Apr. 16, 1987 [CH] Switzerland ............ 1489/87

[51] Int. Cl.$^4$ ............................................. C07D 303/00
[52] U.S. Cl. ................................................... 549/329
[58] Field of Search ...................... 549/329; 568/302

[56] References Cited

U.S. PATENT DOCUMENTS

| 2,802,872 | 8/1957 | Sturzenegger | 549/329 |
| 2,848,496 | 8/1958 | Lacey | 549/329 |
| 3,000,906 | 9/1961 | Hasek et al. | 549/329 |
| 3,271,420 | 9/1966 | Zima | 568/302 |

OTHER PUBLICATIONS

Hel. Chim. Acta., vol. 60, (1977), No. 100, pp. 975–977.

Primary Examiner—James H. Reamer
Attorney, Agent, or Firm—Fisher, Christen & Sabol

[57] ABSTRACT

Process for the reduction of the ketene trimer portion in raw diketene by mixing of the diketene with water, an alcohol, a phenol or a carboxylic acid, and heating the mixture to 50° to 130° C., and then distilling off the diketene.

4 Claims, No Drawings

PROCESS FOR THE REDUCTION OF THE KETENE TRIMER CONTENT IN RAW DIKETENE

BACKGROUND OF THE INVENTION

1. Field of the Invention

The invention relates to a process for reduction of the ketene trimer content in raw diketene.

2. Background Art

It is known that in the dimerization of ketene, besides diketene as the main product, polymer resins and a ketene trimer are also formed. This ketene trimer was identified as 3-acetoxycyclobut-2-ene-1-one and is present in portions up to about 5 percent in the diketene.

It is known further that with heating above 50° C. this ketene trimer tends to strongly exothermic reactions [Helv. Chim. Acta 60 (1977) No. 100, p. 975 (ff)]. This property of entering uncontrolled exothermic reactions upon heating makes the ketene trimer a safety hazard during the production and distillation of diketene.

BROAD DESCRIPTION OF THE INVENTION

The object of the invention is to remove the ketene trimer from the raw diketene in a simple way or to reduce its content.

The invention involves a process which achieves such object. The invention process for the reduction of the ketene trimer portion in raw diketene includes mixing the raw diketene with an amount, which corresponds to the amount of ketene trimer in the diketene, of a compound of the general formula:

$$R(XH)_n$$

wherein R is H, an aliphatic hydrocarbon radical with 1 to 18 C atoms or an aromatic hydrocarbon radical, X is oxygen or sulfur, or XH is a COOH group, and n is 1 or 2, heating the mixture to a temperature of 50° to 130° C., and distilling off the diketene from the mixture.

Water, monohydric or polyhydric alcohols with 1 to 18 C atoms, monovalent or multivalent phenols, thiols, polythiols or carboxylic acids can be used as compound $R(XH)_n$. Specific compounds useful as compound $R(XH)_n$ are, for example:

Alcohols: methanol, ethanol, propanol, heptanol, octadecanol and diethylene glycol.
Phenols: phenol and hydroquinone.
Thiols: butylthiol and octadecanethiol.
Polythiols: 1,3-butyldithiol and 1,10-decanedithiol.
Carboxylic acids: formic acid, acetic acid, oxalic acid, malonic acid and succinic acid.

Preferably, alcohols with 1 to 6 C atoms in the molecule or phenol are used as compound $R(XH)_n$.

A temperature of 50° to 130° C. is suitably maintained for 0.25 to 5 hours. Then the diketene can be distilled off without risk.

In the treatment of the raw diketene with a compound of formula $R(XH)_n$, thermostable butene carboxylic acid derivatives of the formula:

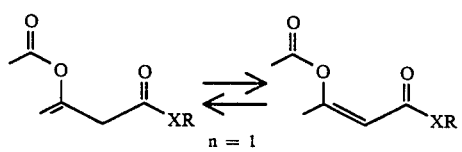

n = 1

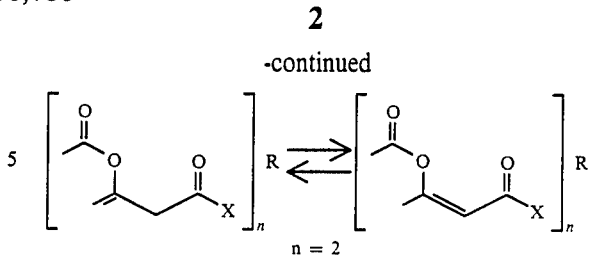

n = 2 are formed.

The process of the invention can be performed in an agitator vessel in a batch process or continuously.

DETAILED DESCRIPTION OF THE INVENTION

As used herein, all parts, percentages, ratios and proportions are on a weight basis, unless otherwise stated herein or otherwise obvious herefrom to one skilled in the art.

EXAMPLE 1

1 kg of diketene raw product, which had a content of 4.2 percent of ketene trimer, was mixed in a thermostatable agitator vessel with the equivalent amount of methanol and heated during 65 minutes to 60° to 63° C. After this treatment, the ketene trimer portion had gone below the detection limit. The raw diketene, practically free of ketene trimer, could be distilled with greatly increased safety.

EXAMPLE 2

0.1 kg of diketene raw product, which had a content of 4.3 percent ketene trimer, was mixed in a thermostatable agitator vessel with the half-molar amount (relative to the ketene trimer) of diethylene glycol and heating during 60 minutes to 60° to 65° C. After this treatment, the ketene trimer content was reduced to 3.1 percent.

EXAMPLE 3

0.1 kg of diketene raw product and 9.22 g of octadecanol were heated within a few minutes to 60° to 65° C. and left at this temperature for 70 minutes. In the cooled sample, the ketene trimer content then amounted to 1.8 percent. This value corresponded to a ketene trimer content reduction of 2.5 percent.

EXAMPLE 4

Similarly to Examples 1 and 3, in two other tests 0.1 kg of diketene raw product was reacted with 3.21 g of phenol or 1.88 g of hydroquinone. The samples cooled to room temperature exhibited the following ketene trimer content reductions:

sample treated with phenol: 0.3 percent of ketene trimer reduction after treatment.

sample treated with hydroquinone: 1.8 percent of ketene trimer reduction after treatment.

EXAMPLE 5

A mixture of 0.1 kg of raw diketene and 9.77 of 1-octadecanethiol was heated within a few minutes to 60° to 65° C. and kept at this temperature for 0.5 hour. A temperature increase to 95° to 100° C. caused a reduction of ketene trimer content of the reaction mixture from 4.8 to 3.3 percent.

EXAMPLE 6

0.1 kg of raw diketene each was mixed in five different batches with 2.38 g of acetic acid, 8.74 g of palmitic acid, 1.77 g of malonic acid, 2.01 g of succinic acid and 4.16 g of benzoic acid (respectively) at room temperature. The mixtures were heated within a few minutes to the reaction temperature. In all cases a reduction of the ketene trimer content was observed as set out in the following table:

| Carboxylic acid | Reaction temperature, (°C.) | Reaction time, (h) | Ketene trimer reduction, percent |
|---|---|---|---|
| acetic acid | 62°–63° | 1.17 | 2.7 |
| palmitic acid | 62° | 1.17 | 2.8 |
| malonic acid | 60°–65° | 1.0 | 4.4 |
| succinic acid | 62°–63° | 1.17 | 3.5 |
| benzoic acid | 62° | 1.17 | 2.8 |

EXAMPLE 7

0.1 kg of diketene raw product was mixed at room temperature with 0.61 g of water and heated within a few minutes to 60° to 65° C. This temperature of the reaction mixture was maintained for a period of 70 minutes. After cooling of the reaction mixture to 20° C., a reduction of the ketene trimer content of the diketene raw product by 3.1 percent resulted.

What is claimed is:

1. Process for the reduction of the ketene trimer portion in the raw diketene, comprising mixing the diketene with an amount, which corresponds to the amount of ketene trimer in the diketene, of a compound of the general formula:

$$R(XH)_n$$

wherein R is H, an aliphatic hydrocarbon radical with 1 to 18 C atoms or an aromatic hydrocarbon radical, X is oxygen or sulfur, or XH is a COOH group, and n is 1 to 2, heating the mixture to temperatures of 50° to 130° C., and distilling off the diketene from the mixture.

2. Process according to claim 1 wherein an aliphatic alcohol with 1 to 18 C atoms is used as compound $R(XH)_n$.

3. Process according to claim 1 wherein phenol or a multivalent phenol, wherein n is 1 or 2, is used as compound $R(XH)_n$.

4. Process according to claim 1 wherein a carboxylic acid wherein n is 1 to 2, and XH is COOH, is used as compound $R(XH)_n$.

* * * * *